United States Patent
Shin et al.

(12)

(10) Patent No.: US 8,514,567 B2
(45) Date of Patent: Aug. 20, 2013

(54) PORTABLE ULTRASONIC DIAGNOSTIC APPARATUS

(75) Inventors: Soo Hwan Shin, Seoul (KR); Mi Ran Song, Seoul (KR); Young Seuk Song, Seoul (KR); Jae Gyoung Kim, Seoul (KR); Sun Ki Lee, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 1033 days.

(21) Appl. No.: 12/491,164

(22) Filed: Jun. 24, 2009

(65) Prior Publication Data
US 2009/0326380 A1    Dec. 31, 2009

(30) Foreign Application Priority Data

Jun. 25, 2008 (KR) .................. 10-2008-0060384

(51) Int. Cl.
*G06F 1/16* (2006.01)
*H05K 5/00* (2006.01)
*A61B 8/00* (2006.01)

(52) U.S. Cl.
USPC .................. 361/679.55; 361/679.01; 600/437

(58) Field of Classification Search
USPC ................................ 600/437, 443, 459, 447; 361/679.01–679.45, 679.55–679.59; 345/156, 345/157, 168, 169
See application file for complete search history.

(56) References Cited

U.S. PATENT DOCUMENTS

| 6,139,496 | A  | * | 10/2000 | Chen et al. ..................... 600/437 |
| 6,636,420 | B2 | * | 10/2003 | Nakano et al. ........... 361/679.27 |
| 7,450,372 | B2 | * | 11/2008 | Lin et al. .................. 361/679.55 |
| 2002/0181193 | A1 | * | 12/2002 | Amemiya et al. ............ 361/683 |
| 2006/0082957 | A1 | * | 4/2006 | Chen ............................. 361/681 |
| 2008/0249406 | A1 | * | 10/2008 | Naruse .......................... 600/437 |
| 2009/0088645 | A1 | * | 4/2009 | Shin et al. ..................... 600/459 |
| 2009/0318779 | A1 | * | 12/2009 | Tran .............................. 600/301 |
| 2010/0121189 | A1 | * | 5/2010 | Ma et al. ....................... 600/437 |
| 2012/0123223 | A1 | * | 5/2012 | Freeman et al. .............. 600/301 |

FOREIGN PATENT DOCUMENTS

| JP | 10-5221 | 1/1998 |
| JP | 2005-517515 | 6/2005 |

OTHER PUBLICATIONS

Japanese Office Action, issued in Japanese Patent Application No. 2009-148806, dated Jul. 19, 2011.

* cited by examiner

*Primary Examiner* — Jayprakash N Gandhi
*Assistant Examiner* — Nidhi Desai
(74) *Attorney, Agent, or Firm* — McDermott Will & Emery LLP

(57) ABSTRACT

Disclosed herein is a portable ultrasonic diagnostic apparatus. The ultrasonic diagnostic apparatus includes a body part, a handle coupled to the body part and having a curved shape, and a display unit coupled to the handle. The handle has a curved shape to improve close contact feelings with an operator's palm, so that an operator does not experience palm fatigue even after extended use.

11 Claims, 8 Drawing Sheets

PORTABLE ULTRASONIC DIAGNOSTIC APPARATUS

CROSS-REFERENCE TO RELATED APPLICATIONS

This Application claims the benefit of Korean Patent Application No. 10-2008-0060384, filed on Jun. 25, 2008, the entire contents of which are incorporated by reference herein.

BACKGROUND OF THE INVENTION

1. Field of the Invention

The present invention relates to an ultrasonic diagnostic apparatus and, more particularly, to a portable ultrasonic diagnostic apparatus.

2. Description of the Related Art

Ultrasonic systems are one of the most widely applied and important diagnostic apparatus. In particular, since the ultrasonic system has characteristics of being non-invasive and non-destructive with respect to a target body, it has been widely used in the medical field. In recent years, a high performance ultrasonic system has been developed to generate two dimensional or three-dimensional interior images of the target body.

Since such an ultrasonic system has a very large size and a heavy weight, it must be secured to a particular location. Further, even in the case of a small size ultrasonic system, it generally has a weight of 10 kg or more, which makes it difficult to move or carry such a small size ultrasonic system. In order to overcome such disadvantages of the ultrasonic system, portable ultrasonic systems have been developed in the related art.

FIG. 1 is a perspective view of a conventional ultrasonic diagnostic apparatus.

Referring to FIG. 1, a conventional ultrasonic diagnostic apparatus 10 includes a body 11, a control panel 12, a display unit 13, and a probe 14.

The body 11 constitutes an outer appearance of the ultrasonic diagnostic apparatus 10 and is driven by power supplied from a battery received therein or from an external power supply. The body 11 is connected to the probe 14 that scans ultrasonic waves and converts the reflected ultrasonic waves into electrical signals, and is provided therein with an electronic circuit that can process analog or digital signals used for ultrasonic diagnosis.

The control panel 12 is disposed on the body 11 and includes a plurality of input units for performing an ultrasonic image pick-up function, a control function, a menu selection function, a measurement and annotation function, and the like.

The display unit 13 receives and displays data and images processed by and sent from the body 11.

The probe 14 includes at least one transducer (not shown). The transducer sends an ultrasonic signal to a target body and receives the ultrasonic signal reflected therefrom.

Such a conventional portable ultrasonic diagnostic apparatus 10 can be reduced in size and weight to be carried easily.

However, since it is inconvenient for an operator to carry such a conventional portable ultrasonic diagnostic apparatus, it is necessary for the operator to have a bag for receiving and carrying the ultrasonic diagnostic apparatus.

Further, since the display unit is secured to the rear side of the body of the conventional portable ultrasonic diagnostic apparatus, it is necessary for an operator to incline his or her body or head to accurately observe an image displayed on a front side of the display unit, thereby causing user inconvenience. Therefore, there is a need for an improved portable ultrasonic diagnostic apparatus.

SUMMARY OF THE INVENTION

The present invention is conceived to solve the above and other problems of the conventional system as described above, and an aspect of the present invention is to provide a portable ultrasonic diagnostic apparatus that can be conveniently carried by an operator and has an improved structure eliminating operator inconvenience, such as the operator having to incline their head or body during the use of the diagnostic apparatus and the like.

In accordance with an aspect of the present invention, a portable ultrasonic diagnostic apparatus includes a body part; a handle coupled to the body part and having a curved shape; and a display unit coupled to the handle.

The body part may include a body disposed inside the handle; and a pedestal disposed outside the body and coupled to the handle.

The pedestal may include a coupling part to which the handle is rotatably coupled.

The coupling part may have a through-hole shape.

The coupling part may include a rolling member to guide rotation of the handle.

The pedestal may further include a securing part to restrict rotation of the handle.

The handle may include a plurality of coupling pieces capable of being separably coupled to each other.

The handle may be detachably coupled to the body part.

The pedestal may be provided with a first fastening part, and the handle may be provided with a second fastening part to be coupled to the first fastening part.

The body part may further include a track ball.

The body part may protrude below the handle.

The portable ultrasonic diagnostic apparatus may further include an assistant device detachably coupled to the handle.

The curved shape may be a circular shape.

BRIEF DESCRIPTION OF THE DRAWINGS

The above and other features and advantages of the present invention will become apparent from the following description of exemplary embodiments given in conjunction with the accompanying drawings, in which.

DETAILED DESCRIPTION OF THE INVENTION

Exemplary embodiments of the present invention will be described in detail with reference to the accompanying drawings hereinafter. For convenience of description, the drawings are not to precise scale and may be exaggerated in thickness of lines or size of components for descriptive convenience and clarity only. Furthermore, terms used herein are defined by taking functions of the present invention into account and can be changed according to the custom or intention of users or operators. Therefore, definition of the terms should be made according to overall disclosures set forth herein.

Figure 1:
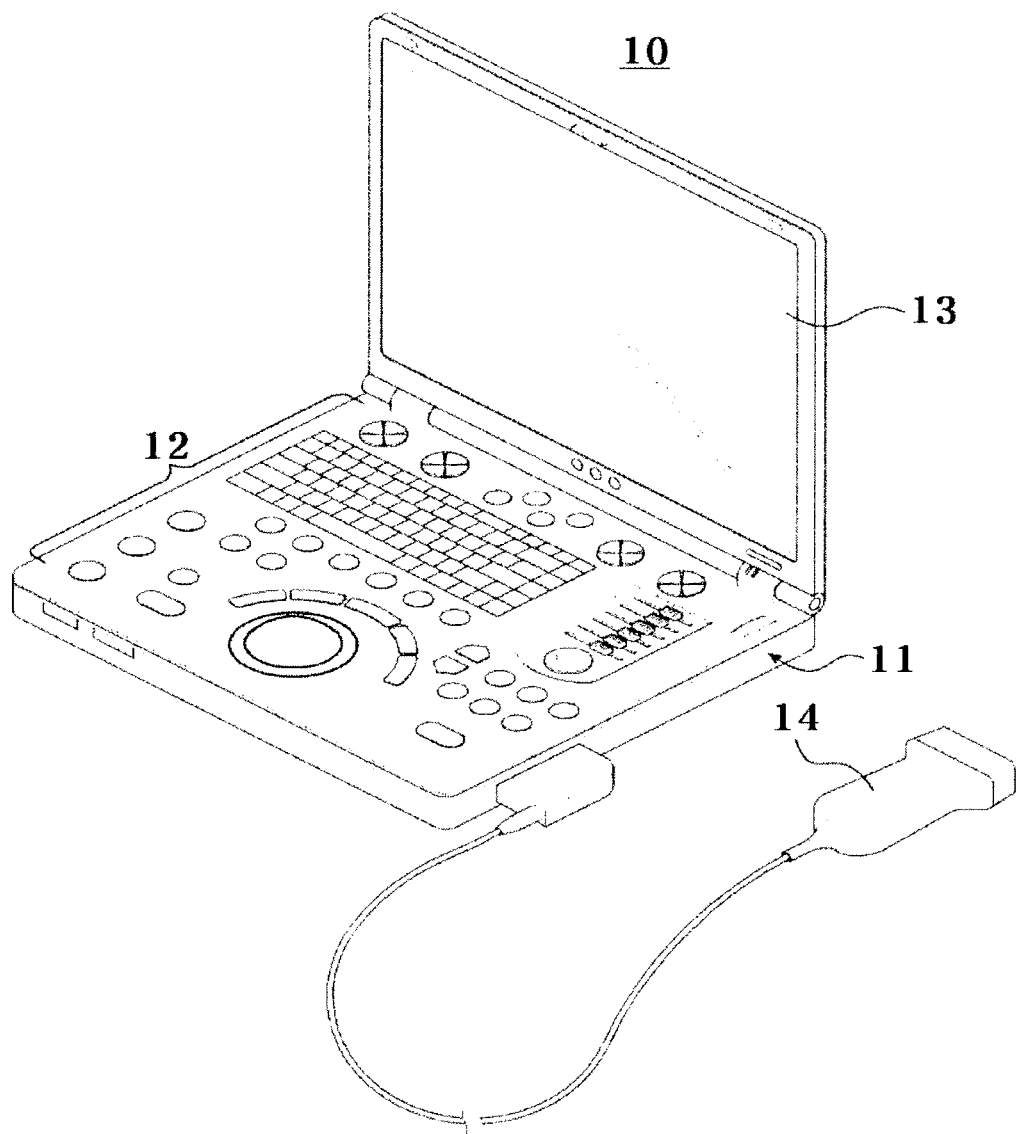
FIG. 1 is a perspective view of a conventional portable ultrasonic diagnostic apparatus.
Figure 2:
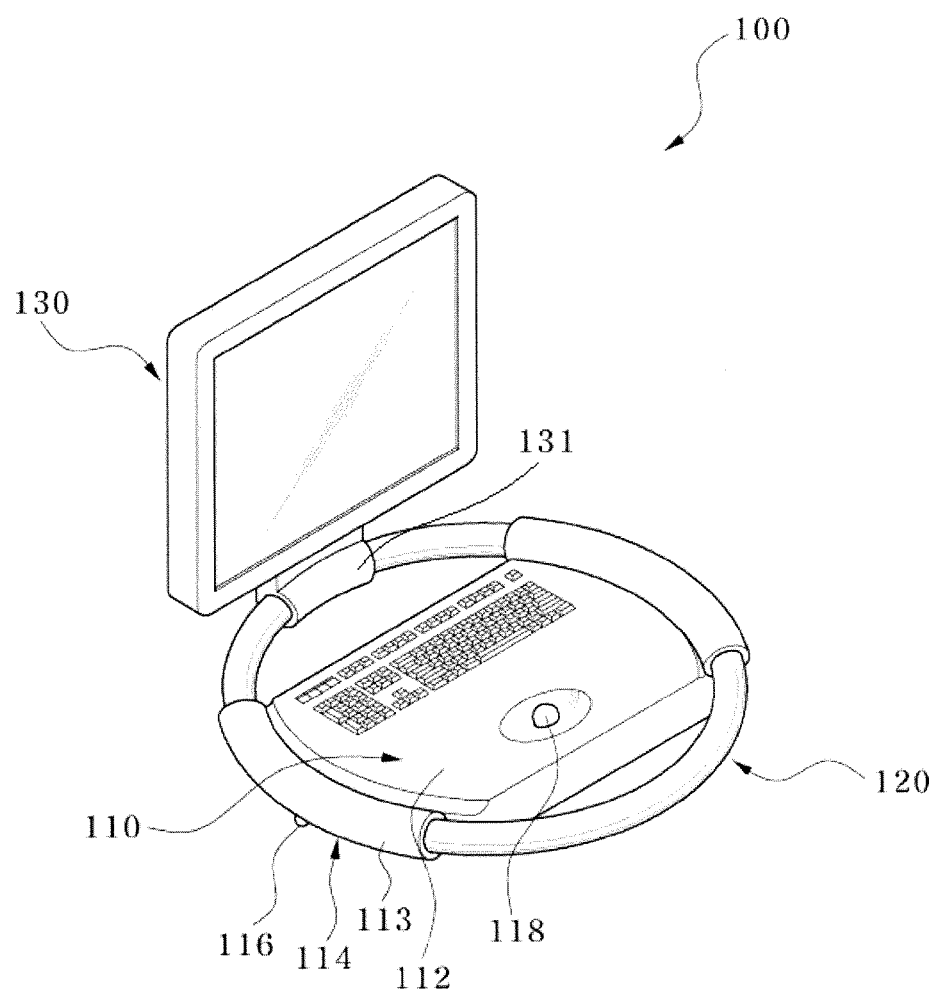
FIG. 2 is a perspective view of a portable ultrasonic diagnostic apparatus according to a first embodiment of the present invention.
Figure 3:
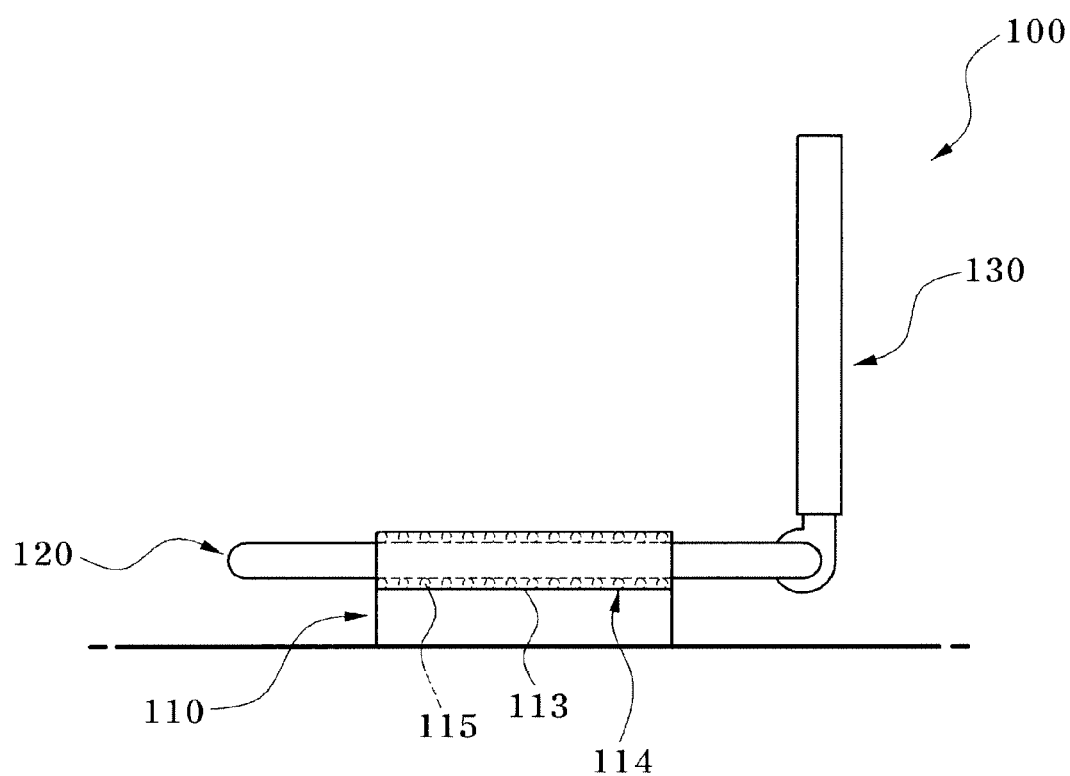
FIG. 3 is a side view of the portable ultrasonic diagnostic apparatus shown in FIG. 2.
Figure 4:
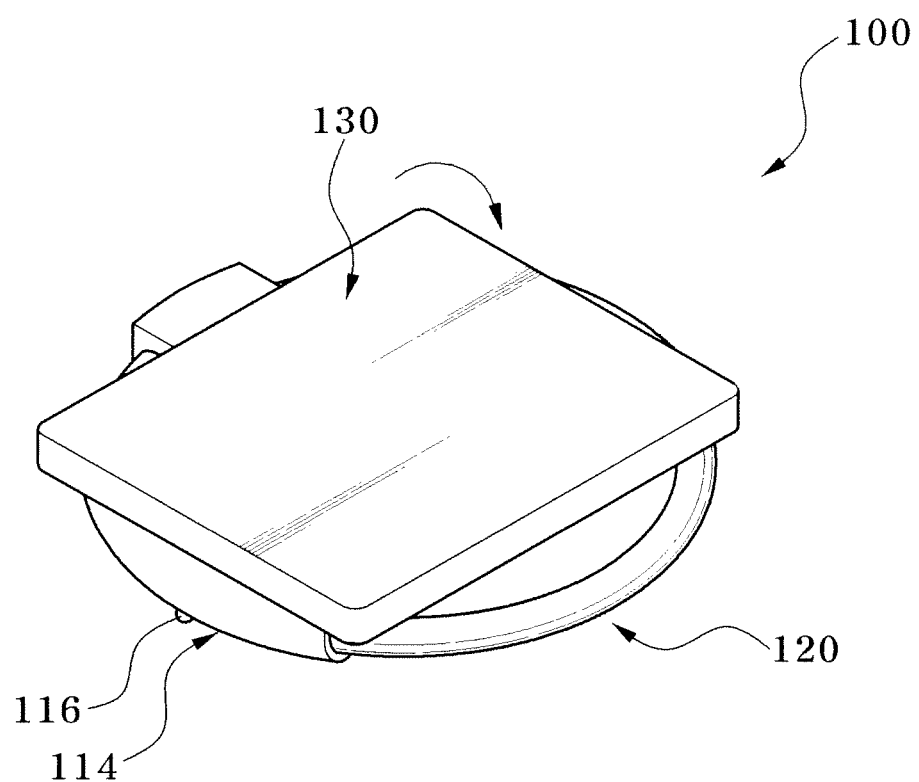
FIG. 4 is a perspective view illustrating a folded state of the portable ultrasonic diagnostic apparatus shown in FIG. 2.
Figure 5:
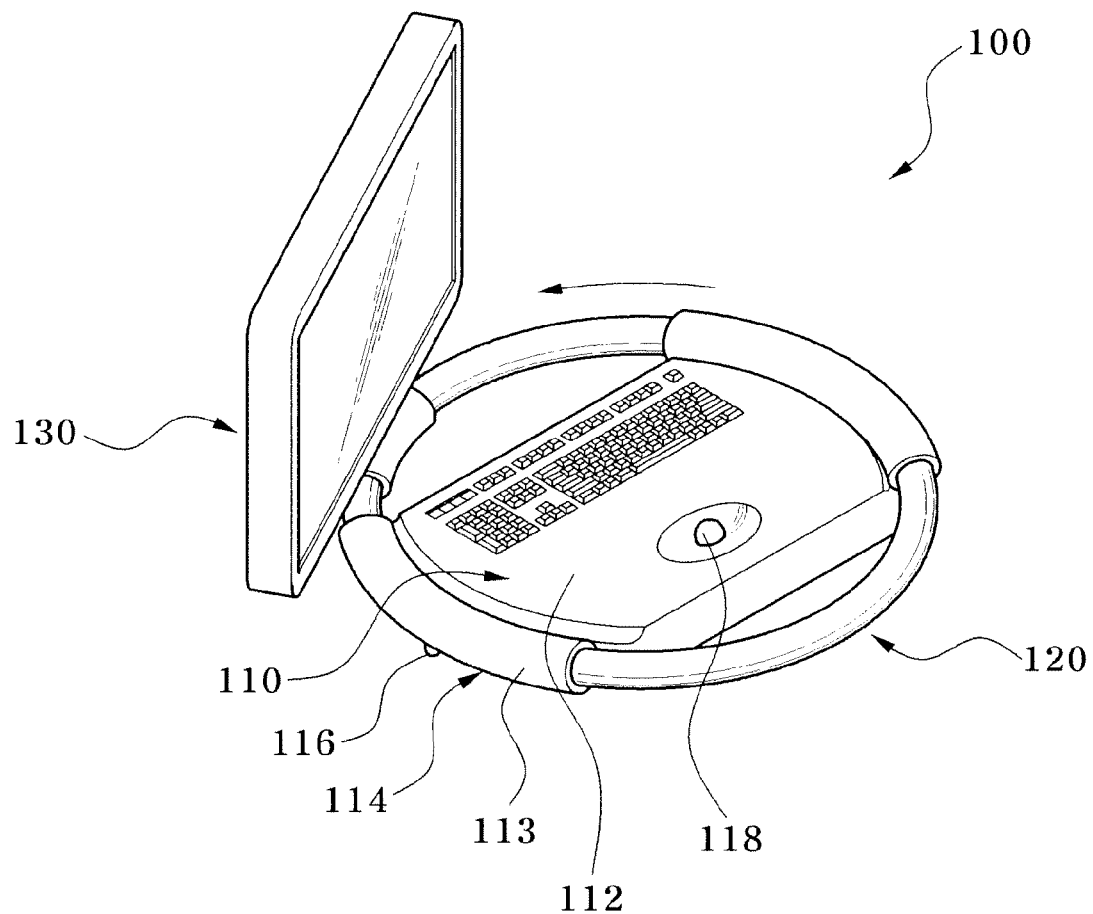
FIG. 5 is a perspective view illustrating a rotating state of the portable ultrasonic diagnostic apparatus shown in FIG. 2.

FIG. 2 is a perspective view of a portable ultrasonic diagnostic apparatus according to a first embodiment of the present invention, FIG. 3 is a side view of the portable ultrasonic diagnostic apparatus shown in FIG. 2, FIG. 4 is a perspective view illustrating a folded state of the portable ultrasonic diagnostic apparatus shown in FIG. 2, and FIG. 5 is a perspective view illustrating a rotating state of the portable ultrasonic diagnostic apparatus shown in FIG. 2.

Referring to FIGS. 2 to 5, the portable ultrasonic diagnostic apparatus 100 according to the first embodiment includes a body part 110, a handle 120, and a display unit 130.

The body part 110 constitutes an outer appearance of the ultrasonic diagnostic apparatus 100, and includes a body 112 and a pedestal 114.

The body 112 includes a beam former for transmit-focusing ultrasonic signals transmitted through a probe (not shown) and for receive-focusing ultrasonic signals received through the probe, a data creator for creating frame data based on the signals output from the beam former, a processor for generating a two-dimensional or three-dimensional interior image of a target body based on the frame data, a storage for storing data, a plurality of operating keys (reference number omitted) for driving the diagnostic apparatus 100 or for selecting functions thereof.

The pedestal 114 is disposed outside the body 112. The pedestal 114 is coupled to the handle 120. The pedestal 114 is provided with a coupling part 113 to which the handle 120 is rotatably coupled. The coupling part 113 has a curved through-hole shape such that the handle 120 can be inserted into and can penetrate the coupling part 113.

The handle 120 is coupled to the body part 110. The handle 120 has a curved shape, and preferably a circular shape. The handle 120 is inserted into the coupling part 113 configured to have the curved through-hole shape corresponding to the shape of the handle 120, so that the handle 120 is rotatably coupled to the pedestal 114.

Although the handle 120 is provided on the body part 110 to rotate 360 degrees, the handle 120 is rotated at a restricted angle since it is coupled to the display unit 130 described below.

The handle 120 can be rotated according to manipulation of an operator. For easy rotation of the handle 120, the body part 110 is configured to protrude below the handle 120.

Further, for more easy rotation of the handle 120, the coupling part 113 may be provided with a rolling member 115 that guides the rotation of the handle 120. Examples of the rolling member 115 include a ball bearing, a roller, and the like.

The display unit 130 is coupled to the handle 120 by a cylindrical hollow fastener 131. The display unit 130 serves to receive and display data and images processed by and sent from the body 112, and is electrically connected to the body 112 through a cable (not shown). Here, the cable connected to the display unit 130 can be connected to the body 112 through the handle 120.

The display unit 130 is coupled to the handle 120 to rotate up or down around the handle 120, so that the display unit 130 can rotate toward the body part 110 to cover the body part 110. The display unit 130 may be fixedly or separably coupled to the handle 120.

Next, operation and effects of the portable ultrasonic diagnostic apparatus 100 according to this embodiment will be described.

For the portable ultrasonic diagnostic apparatus 100 according to this embodiment, the handle 120 is used as a gripper when an operator carries the apparatus 100. In other words, when the operator carries the apparatus 100, the display unit 130 is rotated toward the body part 110 to allow the portable ultrasonic diagnostic apparatus 100 to be folded, and the handle 120 is gripped by the operator for carrying the apparatus 100. In this case, the handle 120 acts as the gripper of the apparatus 100.

Since the handle 120 has a curved shape, it improves close contact feelings with an operator's palm, so that the operator does not experience palm fatigue even after extended use.

The pedestal 114 may be provided with a securing part 116 that restricts rotation of the handle 120. The securing part 116 is configured to selectively restrict the rotation of the handle 120 according to manipulation of the operator. When carrying the ultrasonic diagnostic apparatus 100, the operator can stably carry the apparatus 100 by securing the rotation of the handle 120 by means of the securing part 116 to prevent the apparatus from shaking.

The securing part 116 may be formed in a variety of shapes. For example, the securing part 116 may be configured to restrict the rotation of the handle 120 by means of frictional interaction with the handle 120, or may be configured to restrict the rotation of the handle 120 by means of interaction with a plurality of protrusions formed on the handle 120. A detailed configuration of the securing part 116 can be variously realized by a person having ordinary knowledge in the art, and a detailed description thereof will be omitted herein.

The body part 110 may further include a track ball 118. The track ball 118 is disposed on a location relatively apart from the display unit 130 on the body part 110. For the portable ultrasonic diagnostic apparatus 100 of this embodiment, the handle 120 serves to support the operator's hand when the operator manipulates the track ball 118 or operating keys around the track ball 118. Accordingly, the portable ultrasonic diagnostic apparatus 100 of this embodiment can improve user convenience and reduce hand fatigue.

Further, for the portable ultrasonic diagnostic apparatus 100 of this embodiment, since the handle 120 is rotatably disposed on the body part 110, the display unit 130 coupled to the handle 120 can be rotated by the rotation of the handle 120.

When the operator rotates the handle 120, the display unit 130 rotates along with the handle 120 so that an angle of view of the display unit 130 also rotates. Thus, the operator can rotate the angle of view of the display unit 130 by rotating the handle 120.

With the handle 120 and the display unit 130 configured as described above, the portable ultrasonic diagnostic apparatus 100 of this embodiment enables the operator to view an image displayed on the front side of the display unit 130 simply by manipulating the handle 120 without inclining his or her body or head, even in the event where the operator carries out diagnosis on a patient with the body part 110 of the apparatus located in a diagonal direction with respect to the operator.

Figure 6:
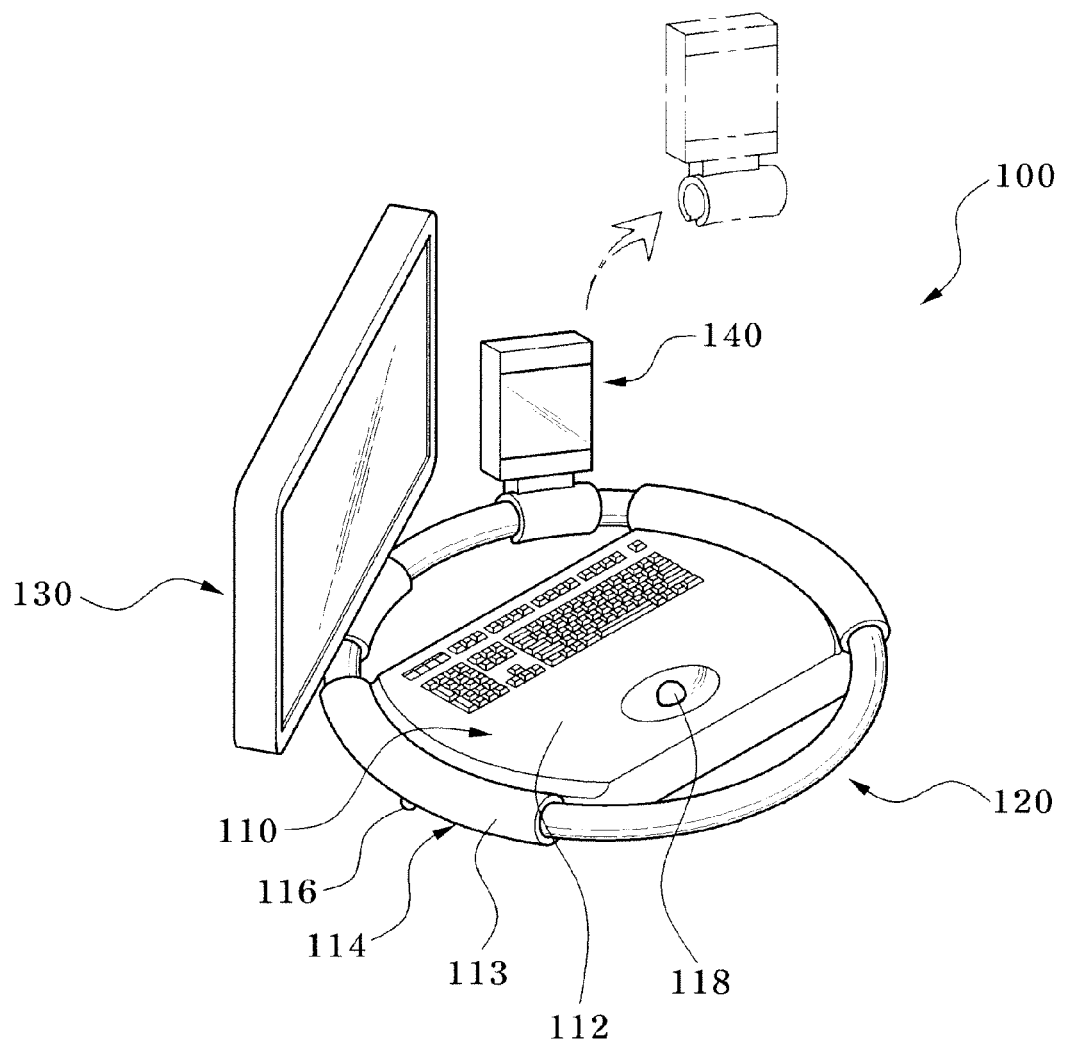
FIG. 6 is a perspective view of the portable ultrasonic diagnostic apparatus shown in FIG. 2, in which an assistant device is coupled to the apparatus.

FIG. 6 is a perspective view of the portable ultrasonic diagnostic apparatus shown in FIG. 2, in which an assistant device is attached to the apparatus.

In FIG. 6, the portable ultrasonic diagnostic apparatus of this embodiment may further include an assistant device 140.

The assistant device 140 may be, but is not limited to, an assistant display, Echo-Printer, a probe holder, a camera, and the like. The assistant device 140 is detachably coupled to the handle 120.

In addition to the aforementioned gripper function and the function of rotating the display unit 130, the handle 120 provides an attaching space for the assistant device 140. Accordingly, the portable ultrasonic diagnostic apparatus 100 of this embodiment allows an operator to attach the assistant device 140 and other accessories to the handle 120, so that the assistant device 140 and other accessories can be used or accommodated in the apparatus as needed.

Figure 7:
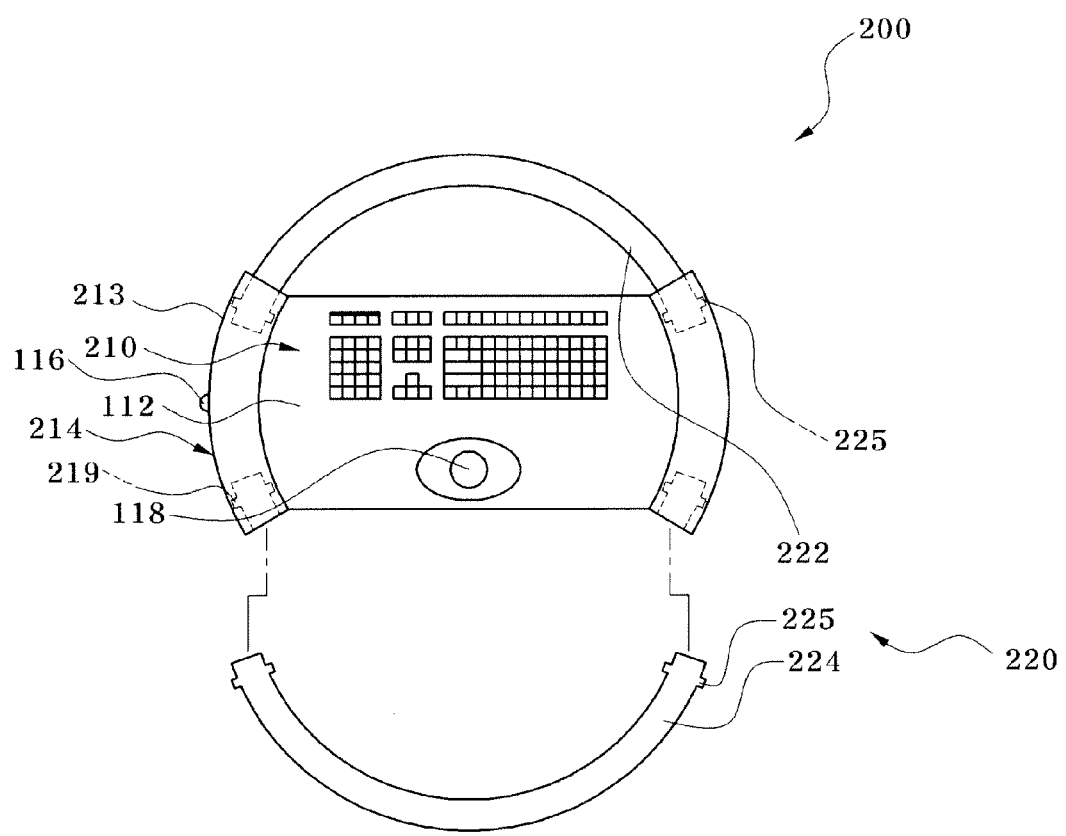
FIG. 7 is a plan view of a portable ultrasonic diagnostic apparatus according to a second embodiment of the present invention.
Figure 8:
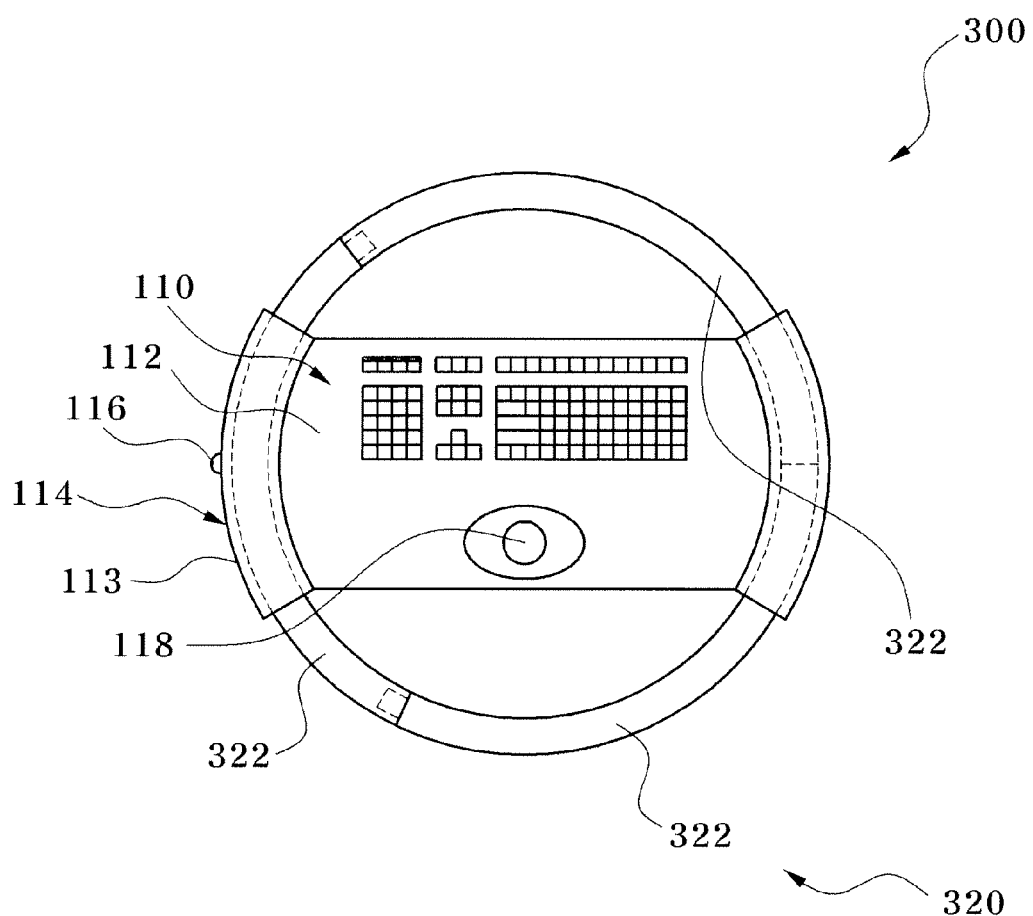
FIG. 8 is a plan view of a portable ultrasonic diagnostic apparatus according to a third embodiment of the present invention.

FIG. 7 is a plan view of a portable ultrasonic diagnostic apparatus according to a second embodiment of the present invention, and FIG. 8 is a plan view of a portable ultrasonic diagnostic apparatus according to a third embodiment of the present invention.

In these drawings, the display unit is not shown for descriptive convenience. Further, the same or similar configurations to those of the aforementioned embodiment are denoted by the same reference numerals, and detailed descriptions thereof are omitted herein.

First, referring to FIG. 7, the portable ultrasonic diagnostic apparatus according to the second embodiment includes a handle 220 detachably coupled to a body part 210.

The handle 220 includes a first handle 222 detachably coupled to one side of a pedestal 214 and a second handle 224 detachably coupled to the other side of the pedestal 214. Further, a coupling part 213 of the pedestal 214 is provided at opposite sides of the coupling part 213 with first fastening parts 219, and the first and second handles 222 and 224 are provided with second fastening parts 225, respectively.

In this embodiment, the first fastening parts 219 are formed in a groove shape and the second fastening parts 225 are formed in a protrusion shape. However, it should be noted that the present invention is not limited thereto and can be modified to a variety of shapes. For example, the first fastening part 219 may be formed in a protrusion shape and the second fastening part 225 may be formed in a groove shape.

According to this embodiment, the first and second handles 222 and 224 can be detachably coupled to both sides of the pedestal 214 by detachably fastening the second fastening part 225 to the first fastening part 219.

With this configuration of the handle 220, the portable ultrasonic diagnostic apparatus 200 of this embodiment can be reduced in volume by separating the handle 220, if needed, thereby providing an advantage of easy custody.

Referring to FIG. 8, the portable ultrasonic diagnostic apparatus 300 of the third embodiment includes a handle 320 detachably coupled to a body part 110.

The handle 320 includes a plurality of coupling pieces 322. The respective coupling pieces 322 are inserted into a coupling part 113 of a pedestal 114 and are separably coupled to each other to constitute the handle 320. In this embodiment, the handle 320 is shown as being constituted by three coupling pieces 322, but the present invention is not limited thereto.

Thus, the handle 320 can be detachably coupled to the body part 10 and can be rotated thereon. With this configuration of the handle 320, the portable ultrasonic diagnostic apparatus 300 has features given by the configuration of the handle that can be rotated on the body part, and by the configuration of the handle that can be separated to several pieces.

As apparent from the above description, the portable ultrasonic diagnostic apparatus according to the present invention includes a handle having a curved shape to improve close contact feelings with an operator's palm, so that the operator does not experience palm fatigue even after extended use.

Further, for the portable ultrasonic diagnostic apparatus of the invention, when an operator carries out diagnosis on a patient with a body part of the ultrasonic diagnostic apparatus located in a diagonal direction with respect to the operator, the operator can view a display unit of the apparatus by a simple operation of rotating the handle, thereby enhancing operating efficiency.

In addition, for the portable ultrasonic diagnostic apparatus of the invention, when the operator manipulates a track ball or an operation key around the track ball, the handle supports the operator's hand, thereby improving conveniences in use while reducing hand fatigue.

Moreover, the portable ultrasonic diagnostic apparatus of the invention is configured to allow an assistant device and other accessories to be attached to the handle such that the assistant device and other accessories can be employed by the operator or can be received in the apparatus.

Although the present invention has been described with reference to the embodiments and the accompanying drawings, it will be apparent to those skilled in the art that the embodiments are given by way of illustration, and that various modifications and equivalent embodiments can be made without departing from the spirit and scope of the present invention. Accordingly, the scope of the present invention should be limited only by the accompanying claims.

What is claimed is:

1. A portable ultrasonic diagnostic apparatus, comprising: a body part including a user input device; a circular-shape handle coupled to and encircling the body part; and a display unit rotatably coupled to a portion of the handle; wherein the body part comprises: a body disposed inside the handle; and at least one pedestal disposed outside the body and coupled to the handle; wherein the at least one pedestal comprises a coupling part to which the handle is rotatably coupled.

2. The portable ultrasonic diagnostic apparatus according to claim 1, wherein the coupling part has a through-hole shape.

3. The portable ultrasonic diagnostic apparatus according to claim 1, wherein the coupling part comprises a rolling member to guide rotation of the handle.

4. The portable ultrasonic diagnostic apparatus according to claim 1, wherein the at least one pedestal further comprises a securing part to restrict rotation of the handle.

5. The portable ultrasonic diagnostic apparatus according to claim 1, wherein the handle comprises a plurality of coupling pieces capable of being separably coupled to each other.

6. The portable ultrasonic diagnostic apparatus according to claim 1, wherein the handle is detachably coupled to the body part.

7. The portable ultrasonic diagnostic apparatus according to claim 6, wherein the at least one pedestal is provided with a first fastening part and the handle is provided with a second fastening part to be coupled to the first fastening part.

8. The portable ultrasonic diagnostic apparatus according to claim 1, wherein the body part further comprises a track ball.

9. The portable ultrasonic diagnostic apparatus according to claim 1, wherein the body part protrudes below the handle.

10. The portable ultrasonic diagnostic apparatus according to claim 1, further comprising: an assistant device detachably coupled to the handle.

11. The portable ultrasonic diagnostic apparatus according to claim 1, further comprising:

a cylindrical hollow fastener attached to a side of the display unit and securing the display unit to the portion of the handle.

\* \* \* \* \*